United States Patent [19]  [11] 4,034,050
Sasaki et al. [45] July 5, 1977

[54] PREPARATION OF 5-METHYL-2-NITROPHENOL

[75] Inventors: Mitsuru Sasaki; Kunio Mukai, both of Nishinomiya, Japan

[73] Assignee: Sumitomo Chemical Company, Ltd., Osaka, Japan

[22] Filed: Dec. 17, 1975

[21] Appl. No.: 641,585

Related U.S. Application Data

[63] Continuation-in-part of Ser. No. 547,090, Feb. 4, 1975, abandoned.

[30] Foreign Application Priority Data

| Jan. 31, 1975 | United Kingdom | 4428/75 |
| Feb. 4, 1975 | Germany | 2504592 |
| Feb. 3, 1975 | France | 75.03304 |
| Feb. 4, 1975 | Belgium | 153032 |
| Feb. 4, 1975 | United Kingdom | 01314/75 |
| Feb. 4, 1975 | Canada | 219387 |
| Feb. 3, 1975 | Italy | 67270/75 |
| Feb. 3, 1975 | U.S.S.R. | 2103873 |
| Feb. 3, 1975 | Switzerland | 1240/75 |
| Feb. 3, 1975 | Denmark | 360/75 |
| Feb. 4, 1975 | Czechoslovakia | 725/75 |

[52] U.S. Cl. .......................................... 260/622 R
[51] Int. Cl.$^2$ ...................................... C07C 79/24
[58] Field of Search ......................... 260/622 R, 622

[56] References Cited

UNITED STATES PATENTS 2,810,767  10/1957  Clarke ........................ 260/622 R
2,985,688  5/1961   Mersch et al. ............... 260/622 R Primary Examiner—James O. Thomas, Jr.
Assistant Examiner—W. B. Lone
Attorney, Agent, or Firm—Wenderoth, Lind & Ponack

[57] ABSTRACT

Process for preparing 5-methyl-2-nitrophenol of high purity by sulfonating tri-m-cresyl phosphate, nitrating the sulfonated tri-m-cresyl phosphate, hydrolyzing the nitrated, sulfonated tri-m-cresyl phosphate to obtain a mixture of nitro-m-cresols, steam-distilling the mixture, and repeatedly washing the distillate with a dilute aqueous alkaline solution.

7 Claims, No Drawings

PREPARATION OF 5-METHYL-2-NITROPHENOL

This application is a continuation-in-part of Ser. No. 547,090 filed Feb. 4, 1975, now abandoned.

The present invention relates to a novel process for preparing 5-methyl-2-nitrophenol which is an important intermediate for preparation of agricultural chemicals. More particularly, the present invention relates to a novel process for preparing high-purity 5-methyl-2-nitrophenol characterized by (1) sulfonating tri-m-cresyl phosphate with a sulfonating agent, (2 nitrating the resulting sulfonated tri-m-cresyl phosphate with a nitrating agent, (3) hydrolyzing the resulting compound to crude nitro-m-cresols, (4) steam-distillating said nitro-m-cresols to obtain, as a distillate, a mixture of 5-methyl-2-nitrophenol and 3-methyl-2-nitrophenol, and then (5) separating 5-methyl-2-nitrophenol from the mixture by repeated washing with an aqueous alkali solution of required concentration.

The objective compound according to the present invention, i.e. 5-methyl-2-nitrophenol, is useful as an intermediate for preparing excellent herbicides, for example, O-ethyl-O-(5-methyl-2-nitrophenyl)-N-sec.-butylphosphoroamidothioate, which can be obtained by reacting O-ethyl-N-sec.-butyl-thiophosphoroamido chloridate with 5-methyl-2-nitrophenol. Said phosphoroamidothioate has low toxicity and is particularly free from delayed neurotoxicity which is characteristic of certain organo-phosphorus compounds, and therefore can be used safely as a herbicide in the field (Dos. No. 2147873).

A large number of reports on the preparation of substituted phenols have been made prior to the present invention, but none of them gives an economical preparation of 5-methyl-2-nitrophenol.

It is well known that various nitro-isomers are prepared by the nitration of substituted phenols with suitable nitrating agents, and that the direct nitration is limited because of side-reactions and poor yields. For example, direct nitration of m-cresol gives, as a mononitro derivative, a mixture of 3-methyl-2-nitrophenol, 3-methyl-4-nitrophenol and 5-methyl-2-nitrophenol, and the total yield of these isomers is very poor (Liebigs Annalen der Chemie, 217, 51 and 259, 250; Berichte der Deutschen Chemischen Gesellschaft, 40, 4322 and 42, 3098).

Furthermore, it is well known that of these isomers 3-methyl-2-nitrophenol and 5-methyl-2-nitrophenol can easily be separated as a mixture from the other isomer by steam-distillation, but the two ortho isomers are very difficult to separate from each other as they are very similar to each other in melting point and other physical and chemical properties as shown below.

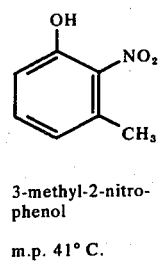
3-methyl-2-nitrophenol
m.p. 41° C.

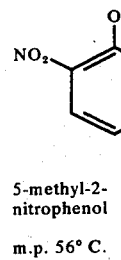
5-methyl-2-nitrophenol
m.p. 56° C.

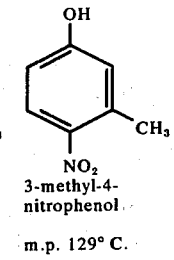
3-methyl-4-nitrophenol
m.p. 129° C.

When the mixture of the two compounds is used as it is for the reaction with O-ethyl-N-sec.-butylthiophosphoroamido chloridate to produce a herbicide, it is apparent that the mixture of a reaction product from 3-methyl-2-nitrophenol and a reaction product from 5-methyl-2-nitrophenol is obtained, as the two compounds show a similar behavior in the reaction. Nevertheless, there is not reported an industrially advantageous method for separating 5-methyl-2-nitrophenol from the mixture.

As a method other than the above-mentioned ones, there is disclosed in Journal of Chemical Society, 24, 1299 that 5-methyl-2-nitrophenol can be prepared by nitration of sulfonated m-cresol in acetic acid, but description as to the yield and purity is not given therein. The inventors traced the method and confirmed that the total yield was very poor due to the direct nitration as mentioned above and that a large amount of 3-methyl-2-nitrophenol was produced as a by-product.

Furthermore, there is disclosed in Journal of Chemical Society, 1277 (1923) that m-cresol is sulfonated with a fuming sulfuric acid and then the resulting sulfonated m-cresol is nitrated with a mixed acid (nitric acid plus sulfuric acid), but by this method 3-methyl-2-nitrophenol is obtained as a main product and only a small amount of 5-methyl-2-nitrophenol is obtained as a by-product, the total yield being very poor for the reason as mentioned above.

It is also reported that 3-methyl-4-nitrophenol was selectively obtained by nitration of tri-m-cresol phosphate and subsequent hydrolysis. (U.S. Pat. No. 2,985,688).

Therefore, the process for preparing high-purity 5-methyl-2-nitrophenol in a high yield is desired at present.

The inventors have studied to develop an advantageous process for preparing 5-methyl-2-nitrophenol, and found that 5-methyl-2-nitrophenol can be obtained in an overall yield of about 60% from tri-m-cresyl phosphate by subjecting sulfonated tri-m-cresyl phosphate to nitration, followed by hydrolysis, steam-distillating the resulting product to obtain a distillate consisting of 90% of 5-methyl-2-nitrophenol and 10% of 3-methyl-2-nitrophenol and then washing the distillate with a dilute aqueous alkali solution.

The process according to the present invention is an industrially very advantageous and economical process, on considering that tri-m-cresyl phosphate used as a starting material is under mass-production on a industrial scale.

The present reaction proceeds according to the following schema:

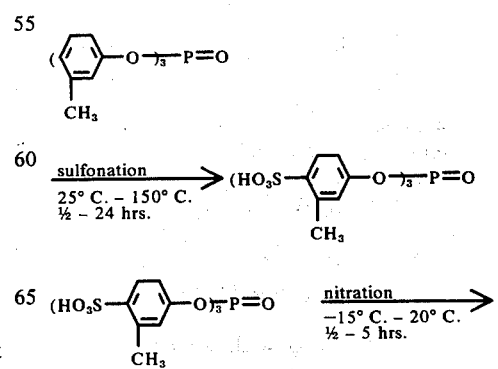

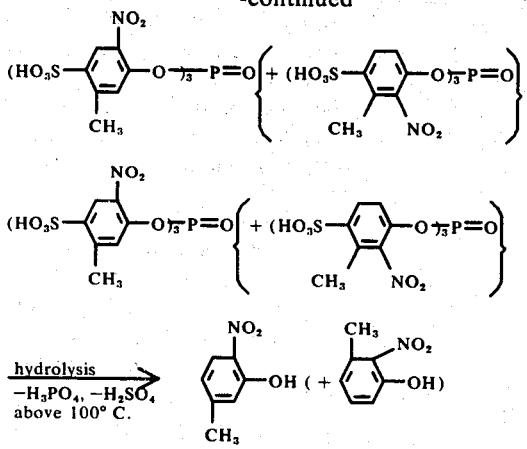

The process according to the present invention will be illustrated in the following in more detail.

Te sulfonating agents to be used in the present invention include sulfuric acid and various fuming sulfuric acids, among which sulfuric acid is preferred. The sulfonation conditions depend upon the particular sulfonating agent used, and the sulfonating reaction may be carried out within a wide temperature range of 25° to 150° C. among which 25° to 100° C. is preferable, and within a wide reaction time of ½ to 24 hours.

However, the specifically controlled sulfonation conditions to obtain tri-m-cresyl phosphate are necessary for highly selective preparation of 5-methyl-2-nitrophenol. For instance, since sulfonation of tri-m-cresyl phosphate does not proceed at low temperature in 96% sulfuric acid, 3-methyl-4-nitrophenol was selectively obtained by direct nitration and subsequent hydrolysis as shown in U.S. Pat. No. 2,985,688.

Furthermore, when the sulfonation is carried out at above 120° C., the ratio of 3-methyl-2-nitrophenol to 5-methyl-2-nitrophenol increases.

The nitrating agents to be used in the present invention include nitric acid, various fuming nitric acid, nitric acid plus sulfuric acid (the so-called mixed acid) and acetic acid plus nitric acid, among which the mixed acid is more preferred. The reaction temperatures and times depend upon the particular nitrating agent used, and are generally −15° to 20° C. (preferably −5° to 5° C.) and ½ to 5 hours, respectively.

For the hydrolysis followed by de-sulfonation, it is desirable to use sulfuric acid, phosphoric acid, conc. hydrochloric acid or a mixture thereof. The temperature and time of the hydrolysis are preferably 110° to 170° C. (more preferably 110° to 130° C.) and 10 to 20 hours, respectively. In the present invention, a continuous process is possible if sulfuric acid is used as a reaction reagent and solvent.

The crude nitrocresols obtained by the hydrolysis can be purified by steam-distillation according to the usual method, and thus 5-methyl-2-nitrophenol and 3-methyl-2-nitrophenol are separated as an azeotropic mixture together with distilled water from the crude nitrocresol. The mixture can be separated from water by cooling and filtering, or by extracting the distillate with an inert organic solvent such as benzene, toluene, ether, chloroform and carbon tetrachloride. The nitro-m-cresol obtained was submitted to gas chromatography for analysis.

The mixture thus obtained usually consists of about 90% of 5-methyl-2-nitrophenol and as a by-product about 10% of 3-methyl-2-nitro-phenol. The by-product can be removed by washing the obtained mixture or the extracted mixture repeatedly with a dilute aqueous alkaline solution. The alkalis to be used include sodium hydroxide, potassium hydroxide, sodium carbonate and potassium carbonate, among which sodium hydroxide is preferred. The concentration of the alkaline solution may vary within a wide range, but it is more preferably 0.1 to 2.0% by weight for the washing at about room temperature. The number of washings depends upon the concentration, and for washing with a 0.8% aqueous alkaline solution, four washings are sufficient to reduce the content of 3-methyl-2-nitrophenol to less than 2% by weight.

By the process described above, the objective compound, 5-methyl-2-nitrophenol, is successfully obtained in a purity of more than 98% and in an overall yield of 55 to 60% from tri-m-cresyl phosphate.

The present invention will be illustrated with reference to the following examples, which are given only for the purpose of illustration and not to limit the scope of the invention.

EXAMPLE 1

To 200 g. of 96% sulfuric acid were added 36.8 g. (0.1 M) of tri-m-cresyl phosphate while stirring, and the resulting mixture was kept at 50° C. for 6 hours. Then, a mixed acid consisting of 28.4 g. of 70% nitric acid and 50.0 g. of 96% sulfuric acid was added dropwise thereto at −5° to 3° C., and the resulting mixture was kept at 2° to 5° C. for 2 hours. After the reaction was completed, the reaction mixture was poured into 150 ml. of ice water, heated to 130° C. and then steam-distilled between 130° to 170° C. while adding dropwise fresh water to make up for the water distilled out. When the temperature reached 170° C., the steam-distillation was stopped. Amount of the distillate thus obtained was 40.0 g. (yield 87.1%). Composition by gas chromatographic analysis:

| | |
|---|---|
| 5-methyl-2-nitrophenol | 83.0 % |
| 3-methyl-2-nitrophenol | 9.1 % |
| 3-methyl-4-nitrophenool | 3.0 % |
| others | 4.9 % |

The distillate was dissolved in 200 g. of toluene and separated, the organic layer was washed three times with 130 ml. portions of a 0.8% aqueous caustic soda solution. Toluene was evaporated to obtain 28.0g. of the objective compound (yield 61.0%). The compound consisted of 98.5% of 5-methyl-2-nitrophenol and 1.5 % of 3-methyl-2-nitrophenol.

EXAMPLE 2

To 100 g. of a 10% fuming sulfuric acid were added 36.8 g. (0.1) M) of tri-m-cresyl phosphate while stirring, during which the temperature rose from 25° to 70° C., and the resulting mixture was allowed to stand overnight at room temperature. Then to the solution was added dropwise at 0° C. a mixed acid of 28.4 g. of 70% nitric acid and 50 g. of conc. sulfuric acid, and the reaction mixture was kept at 2° to 5° C. for 2 hours.

After the reaction was completed, the reaction solution was poured into 150 ml. of ice water, heated to 120° C. and maintained at that temperature for 20 hours while stirring. Then, the resulting solution was cooled and extracted twice with each 150 ml. portions of toluene. The combined extracts were freed of toluene by distillation and steam-distilled at 100° C. to obtain 36.8 g. of distillate (yield 80.2%).

Composition by gas chromatographic analysis:

| 5-methyl-2-nitrophenol | 90.0 % |
| --- | --- |
| 3-methyl-2-nitrophenol | 10.0 % |
| others | 0.0 % |

The distillate was dissolved in 150 ml. of toluene and separated, and the organic layer was washed three times with each 107 ml. portions of a 0.8% aqueous caustic soda solution and then freed of toluene by distillation to obtain 27.0 g. of the objective compound (yield 58.8%). The compound consisted of 99.0% of 5-methyl-2-nitrophenol and 1.0% of 3-methyl-2-nitrophenol.

EXAMPLE 3

To 200 g. of 96% sulfuric acid were added 36.8 g. (0.1 M) of tri-m-cresyl phosphate while stirring, and the resulting mixture was kept at 25° to 30° C. for 24 hours. Then, a mixed acid consisting of 28.4 g. of 70% nitric acid and 50.0 g. of 96% sulfuric acid was added dropwise thereto at −5° to 5° C., and the resulting mixture was kept at 2° to 5° C. for 2 hours.

The reaction mixture was poured into 150 ml. of ice water, heated, and steam-distilled at 100° to 160° C. until no oily distillate was deleted in the steam condensate. The distillate was extracted 3 times with 50 ml. portions of chloroform. The combined chloroform extract was dried over anhydrous sodium sulfate, chloroform was evaporated in vacuo. The yellow residue (41.0 g.) was obtained (yield 89.6%), the composition of which by gas chromatographic analysis was as follows: 5-methyl-2-nitrophenol 85.6%; 3-methyl-2-nitrophenol 8.5%; 3-methyl-4-nitrophenol 4.1%; others 1.8%. The crude mixture was steam-redistilled at 100° C. The distillate was dissolved in 100 ml. of toluene and was washed 3 times with 100 ml. portions of 0.8% aqueous caustic soda solution. Removal of toluene gave pure 5-methyl-2-nitrophenol, 26.0 g.

EXAMPLE 4

To 200 g. of 96% sulfuric acid were added 36.8 g. (0.1 M) of tri-m-cresyl phosphate while stirring, and the resulting mixture was kept at 100° C. for 30 minutes. Then, a mixed acid consisting of 28.4 g. of 70% nitric acid and 50 g. of 96% sulfuric acid was added dropwise thereto at −5° to 3° C., and the resulting mixture was kept at 2° to 5° C. for 2 hours. The reaction mixture was poured into 150 ml. of ice water, heated, and steam-distilled at 130° to 170° C. until no oily distillate was detected in the steam condensate. The amount of the distillate obtained was 39.9 g. (yield 86.9%), the composition of which by gas chromatographic analysis was as follows: 5-methyl-2-nitrophenol 80.1%; 3-methyl-2-nitrophenol 11.1%; 3-methyl-4-nitrophenol 4.8%; others 4.1%.

EXAMPLE 5

To 200 g. of 96% sulfuric acid were added 36.8 g. (0.1 M) of tri-m-cresyl phosphate while stirring, and the resulting mixture was kept at 120° C. for 30 minutes. Nitration and steam-distillation were carried out by the same procedures described in Example 4.

The amount of the distillate obtained was 33.0 g. (yield 72.1%), the composition of which by gas chromatographic analysis was as follows: 5-methyl-2-nitrophenol 72.5%; 3-methyl-2-nitrophenol 23.4%; 3-methyl-4-nitrophenol 2.2%; others 1.9%.

COMPARATIVE EXAMPLE 1

To 200 g. of 76% sulfuric acid were added 36.8 g. (0.1 M) of tri-m-cresyl phosphate at below 15° C. while stirring and the resulting mixture was immediately nitrated with a mixed acid, consisting of 28.4 g of 70% nitric acid and 50 g. of 96% sulfuric acid at −5° to 0° C. after 2 hours, the reaction mixture was poured into 150 ml. of ice water. The resulting mixture was heated and maintained at 120° C. for 20 hours. After cooling, the product was extracted 3 times with 50 ml. portions of chloroform. The combined chloroform extract was dried over anhydrous sodium sulfate, chloroform was evaporated in vacuo. The brown residue (43.6 g.) was obtained (yield 45.0%), the composition of which by gas chromatographic analysis was as follows: 5-methyl-2-nitrophenol 7.0%; 3-methyl-2-nitrophenol 2.0%; 3-methyl-4-nitrophenol 91.0%; others 0.0%.

What we claim is:

1. A process for preparing 5-methyl-2-nitrophenol of the formula

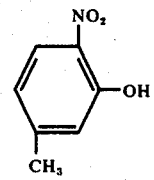

which comprises treating tri-m-cresyl phosphate of the formula

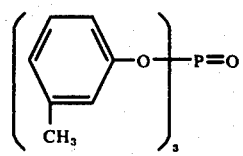

with a sulfonating agent selected from the group consisting of sulfuric acid and fuming sulfuric acid, at a temperature of 25° to 150° C., to form a sulfonated compound of the formula

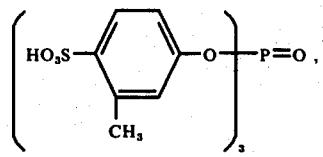

nitrating the sulfonated compound with a nitrating agent selected from the group consisting of nitric acid, fuming nitric acid, a mixture of nitric acid and sulfuric acid and a mixture of acetic acid and nitric acid, at a temperature of −15° to 20° C., to form a nitrated compound of the formula

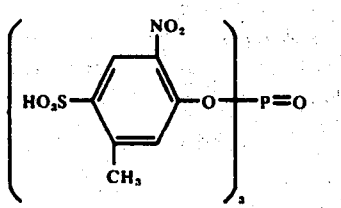

and hydrolyzing the nitrated compound at a temperature of 110° to 170° C. in the presence of an acid selected from the group consisting of sulfuric acid, phosphoric acid, concentrated hydrochloric acid and a mixture of at least two of said acids.

2. The process according to claim 1, wherein the sulfonation reaction is carried out at 25° to 100° C. in the presence of a sulfonating agent selected from the group consisting of concentrated sulfuric acid and 10% fuming sulfuric acid.

3. The process according to claim 1, wherein the nitration reaction is carried out at −5° to 5° C. in the presence of a mixture of nitric acid and sulfuric acid.

4. The process according to claim 1, wherein the hydrolysis reaction is carried out at 110° to 130° C. in the presence of sulfuric acid.

5. The process according to claim 1, wherein the alkaline solution is a solution of sodium hydroxide, potassium hydroxide, sodium carbonate or potassium carbonate.

6. The process according to claim 1, wherein the concentration of the alkaline solution is 0.1 to 2.0% by weight.

7. A process for preparing 5-methyl-2-nitrophenol having a purity greater than 98% which comprises steam-distilling a crude mixture of nitrocresols containing 5-methyl-2-nitrophenol and 3-methyl-2-nitrophenol obtained from the hydrolysis reaction according to claim 1, and washing the distillates with an aqueous alkaline solution.

* * * * *